(12) United States Patent  
Singh (10) Patent No.: US 6,696,483 B2
(45) Date of Patent: *Feb. 24, 2004

(54) INHIBITORS OF ANGIOGENESIS AND TUMOR GROWTH FOR LOCAL AND SYSTEMIC ADMINISTRATION

(75) Inventor: Saira Sayed Singh, Los Gatos, CA (US)

(73) Assignee: OncoPharmaceutical, Inc., Los Gatos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/971,062

(22) Filed: Oct. 3, 2001

(65) Prior Publication Data

US 2002/0061303 A1 May 23, 2002

Related U.S. Application Data

(60) Provisional application No. 60/237,429, filed on Oct. 3, 2000.

(51) Int. Cl.$^7$ .............................................. A61K 31/365
(52) U.S. Cl. ...................... 514/450; 514/457; 514/690; 514/725
(58) Field of Search ................................ 514/450, 690, 514/457, 725

(56) References Cited

U.S. PATENT DOCUMENTS

| | | | |
|---|---|---|---|
| 4,059,457 A | 11/1977 | Austin | |
| 4,062,921 A | 12/1977 | Austin | |
| 4,464,389 A | 8/1984 | Dawson | |
| 4,608,078 A | 8/1986 | Acker et al. | |
| 4,873,092 A | 10/1989 | Azuma et al. | |
| 5,204,107 A | 4/1993 | Tsurutani et al. | |
| 5,242,932 A | 9/1993 | Gandy et al. | |
| 5,439,446 A | 8/1995 | Barry | |
| 5,442,048 A | 8/1995 | Meister et al. | |
| 5,510,418 A | 4/1996 | Rhee et al. | |
| 5,532,221 A | 7/1996 | Huang et al. | |
| 5,536,508 A | 7/1996 | Canal et al. | |
| 5,580,575 A | 12/1996 | Unger et al. | |
| 5,618,837 A | 4/1997 | Hart et al. | |
| 5,637,688 A | 6/1997 | Berglund | |
| 5,696,154 A | 12/1997 | Malspeis et al. | |
| 5,744,155 A | 4/1998 | Friedman et al. | |
| 5,747,475 A | 5/1998 | Nordquist et al. | |
| 5,762,903 A | 6/1998 | Park et al. | |
| 5,773,592 A | 6/1998 | Mills | |
| 5,843,925 A | 12/1998 | Backer et al. | |
| 5,846,952 A | 12/1998 | Vournakis et al. | |
| 5,854,205 A | 12/1998 | O'Reilly et al. | |
| 5,856,315 A | 1/1999 | Backer et al. | |
| 5,871,710 A | 2/1999 | Bogdanov et al. | |
| 5,874,402 A | 2/1999 | Singh et al. | |
| 5,932,545 A | 8/1999 | Henkin et al. | |
| 6,024,688 A | 2/2000 | Folkman et al. | |
| 6,284,751 B1 | 9/2001 | Aiello et al. | |
| 6,287,602 B1 | 9/2001 | Singh | |

FOREIGN PATENT DOCUMENTS

| | | |
|---|---|---|
| WO | WO 92/18116 | 10/1992 |
| WO | WO 93/25225 | 12/1993 |
| WO | WO 96/21438 | 7/1996 |
| WO | 99/31084 | * 6/1999 |

OTHER PUBLICATIONS

Anderson et al., Remington's Pharmaceutical Sciences, 15th Edition, Mack Publishing Co. (1975), pp. 240–245; 1252–1256; pp. 1436–1438; pp. 1461; 1465.*

Grant et al. (1992), "Specific Laminin Domains Mediate endothelial Cell Adhesion, Alignment and Angiogenesis," *Angiogenesis in Health and Disease, Series A: Life Sciences* 227:99–110.

Nicosia et al. (1997), "Endogenous Regulation of Angiogenesis in the Rat Aorta Model," *American Journal of Pathlogy* 151(5):1379–1386.

* cited by examiner

*Primary Examiner*—James H. Reamer
(74) *Attorney, Agent, or Firm*—Reed & Eberle LLP; Karen Canaan (57) ABSTRACT

The invention provides pharmaceutical formulations and methods for the treatment of individuals suffering from a condition, disease, or disorder that is treatable by the inhibition of angiogenesis. The compositions comprise a Golgi apparatus disturbing agent in a substantially nontoxic amount effective to inhibit angiogenesis in a patient in need of anti-angiogenesis therapy, a solvent, and a pharmaceutically acceptable carrier. In preferred formulations, the Golgi apparatus disturbing agent is brefeldin A.

44 Claims, 6 Drawing Sheets

Treated - Tumor Cell Injection Site

No Evidence of Tumor

FIG. 2B

Control - Tumor Cell Injection Site

Clear Evidence of Tumor

INHIBITORS OF ANGIOGENESIS AND TUMOR GROWTH FOR LOCAL AND SYSTEMIC ADMINISTRATION

CROSS-REFERENCE TO RELATED APPLICATION

This application claims priority under 35 U.S.C. §119(e)(1) to U.S. Provisional Application Ser. No. 60/237,429, filed Oct. 3, 2000.

TECHNICAL FIELD

This invention relates to formulations containing pharmacologically active agents, solvents, carriers, and the like. More particularly, the invention relates to compounds and formulations that have anti-angiogenic effects.

BACKGROUND

The circulatory system serves an important role in the transport of nutrients, proteins, hormones, and other vital molecules that are necessary to maintain life. Blood vessels, which form an intricate network of pathways, represent an integral component of the circulatory system. In mammalian species, the internal surface of a blood vessel lumen is comprised of endothelial cells. These endothelial cells impart a smooth and low resistance quality to the lumenal surface. Critical to the free flow and transport of blood and blood constituents, the smooth and nonadhesive internal surface of the blood vessel increases the ease with which fluid flows. Without a smooth internal surface, blood vessels would become obstructed due to the formation of thrombi or other blockages at "sticky" locations on the internal walls. Complete or even partial blood vessel blockage would cause restriction of blood flow, thereby compromising the viability of living tissue served by the vessel. Thus, endothelial cells represent an important structural component of blood vessels and also provide blood vessels with a smooth internal surface.

The formation of blood vessels in vivo takes place in response to stimuli, which are provided in the form of specialized growth factors. These growth factors induce mitosis in cells already present in blood vessels. The new cells may replace nearby damaged cells, or the new cells may arrange themselves such that new blood vessels are formed. The process of growing blood vessels from endothelial cells is termed "angiogenesis," which results in, among other characteristics, the vascularization of tissue.

Angiogenesis has become a central theme in promoting our understanding of how tissue grows. As indicated above, endothelial cell proliferation is not only desirable, but also necessary to carry out a number of physiological processes, for example the in utero formation of tissues and organs. In other contexts, however, angiogenesis may be harmful to the overall health of an organism. For example, continuous or uncontrolled angiogenesis can cause or exacerbate diseases such as rheumatoid arthritis, psoriasis, and certain retinopathies, e.g., diabetic retinopathy. Furthermore, angiogenesis makes tumor growth and metastasis possible by vascularizing the tumor, thereby supplying the tumor with blood and nutrients that are necessary to sustain the tumor's growth, as well as providing routes by which tumor cells can migrate to distant parts of the body. Folkman (1986) *Cancer Res.* 46(2):467–473. Clearly then, the prevention or reduction of angiogenesis may be a desirable goal in treating some disorders and diseases. Compounds have been tested for their ability to inhibit or reduce angiogenesis. Inhibitors of vascular endothelial growth factor (VEGF), a protein that selectively induces mitosis of vascular endothelial cells, have been investigated. For example, U.S. Pat. No. 6,284,751 to Aiello et al. describes using inhibitors of the β isozyme of protein kinase C to counteract the effects of VEGF. Antibiotics such as minocycline have also been reported to inhibit angiogenesis. Some investigators have reported inhibition of tumor growth as well as reduction in the number of metastatic tumors following administration of minocycline in combination with radiation or chemotherapy. See Tamargo et al. (1991) *Cancer Res.* 51(2):672–675, and Teicher (1992) *Cancer Res.* 52(23):6702–6704. U.S. Pat. No. 5,843,925 to Backer et al. describes inhibition of angiogenesis upon administration of certain deoxytetracylines. Many of these angiogenesis-inhibiting compounds, however, have only been tested in vitro for their antiproliferative activity.

Thus, there remains a need to identify additional angiogenesis-inhibiting compounds that have demonstrated in vivo efficacy.

Brefeldin A (BFA) is a macrocyclic lactone first described by Haerri et al. See Haerri et al. (1963) *Chem. Abs.* 59:5726 h. Brefeldin A was also reported to have anti-viral properties, according to Tamura et al. (1968) *J. Antibiotics* 21:161–166. In recent years, brefeldin A has been studied extensively as a protein transport inhibitor. It is believed that brefeldin A can reversibly disrupt the Golgi apparatus, thereby affecting protein transport through the cytoplasm. Domes et al. (1989) *J. Cell Biol.* 109:61–72; Lippincott-Schwartz et al. (1991) *J. Cell Biol.* 112:567–577. It is now known that brefeldin A induces retrograde membrane transport from the Golgi apparatus to the endoplasmic reticulum (ER). Dinter et al. (1998) *Histochem. Cell Biol.* 109:571–590. Currently, brefeldin A is used by researchers primarily as a tool by which to interfere with the processing and sorting of finished proteins in order to more fully understand protein trafficking.

Due to its perceived lack of solubility as well as its resultant toxicity, brefeldin A has not yet been used clinically as an active agent in a pharmaceutical formulation. U.S. Pat. No. 4,608,078 to Acker et al. reported preparation of derivatives of brefeldin A with enhanced solubility, but these derivative compounds still exhibited toxicity due to inadequate solubility. In 1997, the preparation and antitumor activity of water-soluble derivatives of brefeldin A were disclosed in U.S. Pat. No. 5,696,154 to Malspeis et al. These derivatives were claimed to be suitable for intravenous delivery to animals and humans. However, these analogs have only been tested in vitro using minute quantities, which may be insufficient to produce desired therapeutic effects in vivo. U.S. Pat. No. 6,287,602 to Singh describes formulations comprising a Golgi apparatus disturbing agent as the active agent; a biocompatible carrier to increase the effective solubility of the active agent in the formulation and/or to provide a desired sustained release profile of the active agent; and a solvent. Formulations that lack a biocompatible carrier as well as those that are effective in inhibiting angiogenesis, however, are not disclosed.

Thus, there is a need to identify additional compounds as inhibitors of angiogenesis. Furthermore, there remains a need for additional formulations comprising Golgi apparatus disturbing agents for the treatment of disease. The current invention is directed to address these and other needs in the art by providing, inter alia, brefeldin A and related compounds as active agents in methods and formulations for inhibiting angiogenesis.

SUMMARY OF THE INVENTION

Accordingly, it is a primary object of the invention to provide a method for inhibiting angiogenesis in a patient by administering an effective angiogenesis-inhibiting amount of a Golgi apparatus disturbing agent to the patient.

It is yet another object of the invention to provide such a method wherein the Golgi apparatus disturbing agent is administered to a patient in need of anti-angiogenic therapy.

It is still another object of the invention to provide such a method wherein the Golgi apparatus disturbing agent is administered via injection, either systemically or locally.

It is a further object of the invention to provide a pharmaceutical formulation to treat a patient in need of anti-angiogenic therapy, wherein the formulation is comprised of a solvent, a pharmaceutically acceptable carrier, and a Golgi apparatus disturbing agent in a substantially noncytotoxic quantity effective to inhibit angiogenesis.

Additional objects, advantages, and novel features of the invention will be set forth in part in the description that follows, and in part, will become apparent to those skilled in the art upon examination of the following, or may be learned by practice of the invention.

In a first embodiment, then, a pharmaceutical formulation is provided comprising: a Golgi apparatus disturbing agent in a substantially noncytotoxic amount effective to inhibit angiogenesis in a patient in need of anti-angiogenic therapy; a solvent; and a pharmaceutically acceptable carrier. The Golgi apparatus disturbing agent may be any agent known to interfere with the functioning of the Golgi apparatus. Such Golgi apparatus disturbing agents include, without limitation, brefeldin A, nocodazole, ilimaquinone, bafilamycin, okadaic acid, retinoic acid, and combinations thereof. It is preferred, however, that the Golgi apparatus disturbing agent is brefeldin A.

The formulation must contain an amount of the Golgi apparatus disturbing agent that is effective to inhibit angiogenesis. Moreover, the amount used of the Golgi apparatus disturbing agent must not induce substantial cellular death as a result of cytotoxicity. As will be described below in further detail, substantial cellular death caused by cytotoxic quantities of Golgi apparatus disturbing agents is induced by the affected cells' resultant inability to package and/or transport vital proteins intracellularly. In contrast, the inhibition of angiogenesis causes cell death, specifically that of tumor cells, due to a lack of vascularization.

Preferably, the pharmaceutical formulation contains an amount of the Golgi apparatus disturbing agent, e.g., brefeldin A, in a unit dosage form representing from about 0.0001 to about 200 mg/kg (milligrams drug per kilogram body weight of patient), more preferably from about 0.0001 to about 120 mg/kg, still more preferably from about 0.0001 mg to about 15 mg/kg, yet still more preferably from about 0.5 mg to about 15 mg/kg, with from about 1 mg to about 13 mg/kg being most preferred. It is noted that a substantially cytotoxic dose for one species of patient may not be substantially cytotoxic for another.

The solvent may be aqueous or nonaqueous and may also be organic or inorganic. The solvent, however, must be pharmaceutically acceptable and must solubilize at least a portion of the active agent, i.e., the Golgi apparatus disturbing agent.

As the formulations may be injected, either locally or systemically, the pharmaceutically acceptable carrier is preferably suitable for use in injection. Examples of preferred carriers include sodium chloride solutions, lactated Ringer's solution, water, dextrose solutions, and combinations thereof. Additional components may also be included in the pharmaceutical formulation as will be described in more detail below.

In another embodiment, a method for treating a patient is provided comprising administering an angiogenesis-inhibiting amount of a Golgi apparatus disturbing agent to a patient. Although the method may be used to treat any patient who would benefit from inhibition of angiogenesis, the present method is particularly useful to treat individuals suffering from psoriasis, rheumatoid arthritis, retinopathy, and cellular proliferative diseases such as sarcomas, carcinomas, brain cancer, bladder cancer, breast cancer, colorectal cancer, head and neck cancer, liver cancer, myeloma, prostate cancer, and ovarian cancer. The method of treatment involves injecting the pharmaceutical formulation directly or nearly directly into the target site (e.g., an area exhibiting cellular proliferative disease).

DETAILED DESCRIPTION OF THE INVENTION

I. Overview and Definitions

Before describing the present invention in detail, it is to be understood that unless otherwise indicated, this invention is not limited to specific formulation components, manufacturing methods, dosage regimens, or the like, as such may vary. It is also to be understood that the terminology used herein is for the purpose of describing particular embodiments only, and is not intended to be limiting.

It must be noted that, as used in this specification and the appended claims, the singular forms "a," "an," and "the" include plural referents unless the context clearly dictates otherwise. Thus, for example, reference to a "solvent" includes a single solvent, as well as two or more solvents; reference to "an active agent" includes a single active agent, as well as two or more active agents; and so forth.

In describing and claiming the present invention, the following terminology will be used in accordance with the definitions set forth below.

The terms "active agent," "pharmacologically active agent" and "drug" are used interchangeably herein to refer to a chemical compound that induces a desired pharmacological, physiological effect. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent" and "drug" are used, then, it is to be understood that applicant intends to include the active agent per se as well as pharmaceutically acceptable, pharmacologically active salts, esters, amides, prodrugs, metabolites, analogs, etc.

The term "cellular proliferative disease" is intended to refer to any condition characterized by the undesired propagation of cells. Included are conditions such as neoplasms, cancers, and tumors. "Cellular proliferative diseases" also include non-cancerous conditions such as benign melanomas, benign prostatic hyperplasia, psoriasis, and other cellular growths occurring within the epidermal layers.

The term "sustained release" as used herein refers to a drug formulation that provides for gradual release of a drug over an extended period of time, and that preferably, although not necessarily, results in substantially constant drug levels at the desired site over an extended period of time.

By the terms "effective amount" or "therapeutically effective amount" of an agent as used herein are meant a sufficient amount of the agent to provide the desired therapeutic effect. Furthermore, an "effective angiogenesis-inhibiting amount" of an agent is a sufficient amount of the agent to at least partially inhibit angiogenesis. Of course, undesirable effects, e.g., side effects, are sometimes manifested along with the desired therapeutic effect; hence a practitioner balances the potential benefits against the potential risks in determining what is an appropriate "effective amount." As will be pointed out below, the exact amount required will vary from subject to subject, depending on the species, age, and general condition of the subject, mode of administration, and the like. Thus, it is not possible to specify an exact "effective amount." However, an appropriate "effective amount" or "effective angiogenesis-inhibiting amount" in any individual case may be determined by one of ordinary skill in the art using only routine experimentation.

By "pharmaceutically acceptable" carrier is meant a pharmaceutical vehicle comprised of a material that is not biologically or otherwise undesirable, i.e., the material may be administered to an individual along with the selected active agent without causing any undesirable biological effects or interacting in a deleterious manner with any of the other components of the pharmaceutical formulation in which it is contained. Carriers may include excipients and other additives such as diluents, detergents, coloring agents, wetting or emulsifying agents, pH buffering agents, preservatives, and the like.

Similarly, a "pharmacologically acceptable" salt, ester, amide, prodrug, or derivative of a compound as provided herein is a salt, ester, amide, prodrug, or derivative that is not biologically or otherwise undesirable.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically w symptomatic individual by inhibiting or causing regression of a disorder or disease. Thus, for example, the present method of "treating" a patient in need of anti-angiogenic therapy encompasses both prevention of a condition, disease, or disorder that is responsive to anti-angiogenic therapy and treatment of a condition, disease, or disorder that is responsive to anti-angiogenic therapy in a clinically symptomatic individual.

"Optional" or "optionally" means that the subsequently described circumstance may or may not occur, so that the description includes instances where the circumstance occurs and instances where it does not.

"Patient" as used herein refers to a mammalian, preferably human, individual who can benefit from the pharmaceutical formulations and methods of the present invention. There is no limitation on the type of mammal that could benefit from the presently described pharmaceutical formulations and methods.

II. The Pharmaceutical Formulation

In a first embodiment, the invention provides a pharmaceutical formulation for treating a patient in need of anti-angiogenic therapy comprising a Golgi apparatus disturbing agent in a substantially noncytotoxic amount effective to inhibit angiogenesis, a solvent, and a pharmaceutically acceptable carrier. In the context of Golgi apparatus disturbing agents, a "substantially noncytotoxic amount" generally represents an amount insufficient to substantially disrupt intracellular protein transport or packaging in a patient's cells, which would thereby cause substantial cellular death. "Substantial cellular death" in the present context means that upon exposure to an amount of the agent, many living cells, for example, greater than 50%, more preferably greater than 80%, and most preferably greater than 95%, die. Although previously described formulations of Golgi apparatus disturbing agents have emphasized the necessity of adding a biocompatible polymeric carrier in order to address solubility problems and/or provide sustained-release profiles for these agents, it has now been surprisingly discovered that such biocompatible polymeric carriers are not necessary for making pharmaceutically acceptable formulations.

A. Active Agent

It has been surprisingly discovered that the macrocyclic lactone, brefeldin A, a Golgi apparatus disturbing agent, has the ability to inhibit angiogenesis at certain concentrations. Thus, other Golgi apparatus disturbing agents and macrocyclic lactones are also believed to have the same anti-angiogenic effect. Macrocyclic lactones other than brefeldin A are known to those of skill in the art and include, without limitation, acaricides, avermectins, azalides, bredinin, bryostatin 1, chivosazol A, copiamycin, desertomycin, difficidin, doramectin, eprinomectin, geldanamycin, grahamimycins, ivermectin, lincomycin, mathemycin B, megovalicins, moxidectin, oocydin A, oxydifficidin, radicicol, rapamycin, rhizoxin, sirolimus, sporaviridin, streptogramin, tolytoxin, and virginiamycin.

It is particularly preferred that the active agent incorporated in the present invention be a Golgi apparatus disturbing agent. Golgi apparatus disturbing agents include those agents that have the ability to disrupt the entire Golgi network or simply to block one of the network's protein trafficking pathways. The effects of many Golgi apparatus disturbing agents are reversible; that is, once the agent is removed, the Golgi apparatus again functions normally. Although it is not entirely clear how Golgi apparatus disturbing agents interfere with the processing and sorting of finished proteins, much is known about the Golgi apparatus itself. The Golgi apparatus is found in all eukaryotic cells and is responsible for receiving proteins from the endoplasmic reticulum. Upon arriving at the Golgi apparatus, the proteins are modified and/or sorted for delivery to required locations within the cell. For example, the Golgi apparatus is responsible for adding sulfates to the amino acid tyrosine in certain proteins, as well as for cleaving various protein precursors to yield mature hormones and neurotransmitters.

Although any Golgi apparatus disturbing agent may be included in the present formulations, preferred Golgi apparatus disturbing agents include those selected from the group consisting of brefeldin A, nocodazole, ilimaquinone, bafilamycin, okadaic acid, retinoic acid, and combinations thereof. Most preferably, however, the Golgi apparatus disturbing agent is brefeldin A.

Golgi apparatus disturbing agents (or any other active agent) may be present in the formulation as a salt, ester, amide, prodrug, or other derivative, or may be functionalized in various ways as will be appreciated by those skilled in the art and as described in the pertinent texts, patents, and literature; it is preferred, however, that the formulation contain brefeldin A per se, not a derivatived or functionalized form. The active agent of the present invention can either be synthesized using techniques well known in the art or obtained from commercial suppliers.

Golgi apparatus disturbing agents (or any other active agent) may be present in the formulation in the form of a salt, ester, amide, prodrug, derivative, or the like, provided that the salt, ester, amide, prodrug, or derivative is pharmacologically acceptable as well as effective at inhibiting angiogenesis. Salts, esters, amides, prodrugs, and other derivatives of the active agent may be prepared using standard procedures known to those skilled in the art of synthetic organic chemistry, and described, for example, by J. March, Advanced Organic Chemistry: Reactions Mechanisms and Structure, 4th Ed. (New York: Wiley-Interscience, 1992). For example, acid addition salts are prepared from the free base using conventional methodology, which involves reaction with a suitable acid. Generally, the base form of the drug is dissolved in a polar organic solvent such as methanol or ethanol and the acid is added thereto. The resulting salt either precipitates spontaneously or may be brought out of solution by the addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, ethanesulfonic acid, ethanesulfonic acid, p-toluenesulfonic acid, salicylic acid, and the like; as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as those that may be prepared using hydrochloric or hydrobromic acids. Conversely, preparation of basic salts of acid moieties that may be present on a active agent molecule are prepared in a similar manner using a pharmaceutically acceptable base such as sodium hydroxide, potassium hydroxide, ammonium hydroxide, calcium hydroxide, trimethylamine, or the like. Particularly preferred basic salts herein are alkali metal salts, e.g., sodium salts and copper salts. Preparation of esters involves functionalization of hydroxyl and/or carboxyl groups that may be present within the molecular structure of the drug. The esters are typically acyl-substituted derivatives of free alcohol groups, i.e., moieties that are derived from carboxylic acids of the formula R—COOH where R is hydrocarbyl, e.g., alkyl, and preferably lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The amount of active agent in the formulation is preferably a relatively low, effective single unit dose that may be repeatedly administered over time, e.g., over a period of days, weeks, or months. Of course, the actual amount in any unit dose and the administration schedule will depend upon a number of factors, such as the patient and the type of condition, disease, or disorder that is responsive to inhibition of angiogenesis. The amount of the active agent, however, is a quantity that is effective to inhibit angiogenesis, but insufficient to cause substantial cellular death by a direct cytotoxic mechanism, in contrast to cellular death as a result of inhibition of angiogenesis. In the context of Golgi apparatus disturbing agents, the required amount at least partially inhibits the formation of new blood vessels, but is insufficient to cause significant cellular death as a consequence of intracellular disruption of protein transport or packaging.

Those of ordinary skill in the art can readily determine whether any given amount of the Golgi apparatus disturbing agent is a substantially noncytotoxic amount effective to cause inhibition of angiogenesis. For example, mature patients receiving a systemically administered cytotoxic amount of the active agent exhibit generalized systemic toxic effects, including cellular and tissue death, since such an amount is toxic to all cells at all times. In contrast, mature patients receiving a substantially noncytotoxic amount effective to inhibit angiogenesis do not exhibit generalized systemic toxicity, since angiogenesis directly involves only certain cells, e.g., endothelial cells, but manifests only relatively localized effects. In addition, biological samples obtained from, for example, a biopsy, can be stained and analyzed under a microscope to determine whether inhibition of angiogenesis or generalized cellular death is taking place in response to any given dose. Thus, those of ordinary skill in the art can determine effective noncytotoxic angiogenesis-inhibiting amounts of the active agents described herein.

Preferably, the effective angiogenesis-inhibiting amount of the active agent, e.g., brefeldin A, represents from about 0.0001 mg to about 200 mg active agent per kilogram body weight of the patient, more preferably from about 0.0001 to about 120 mg active agent per kilogram body weight of the patient, still more preferably from about 0.0001 mg to about 15 mg active agent per kilogram body weight of the patient, yet still more preferably from about 0.5 mg to about 15 mg active agent per kilogram body weight of the patient, and most preferably from about 1 mg to about 13 mg active agent per kilogram body weight of the patient. In terms of weight percent, the formulations will preferably comprise the active agent, e.g., brefeldin A, in an amount of from about 0.0001 wt. % to about 10 wt. %, more preferably from about 0.001 wt. % to about 1 wt. %, and most preferably from about 0.01 wt. % to about 0.5 wt. %.

B. Solvent

The Golgi apparatus disturbing agent is present in a pharmaceutically acceptable solvent. Suitable solvents include, without limitation: alcohols, e.g., monohydric alcohols such as 1-butanol, 2-butanol, 3-methyl-1-butanol, 2-methyl-1-propanol, and ethanol, as well as polyhydric alcohols such as propylene glycol; ethyl ether; ethyl formate; ethyl acetate; methyl acetate; isobutyl acetate; isopropyl acetate; methylethyl ketone; dimethylacetamide (DMA); 1,1-dimethyloxymethane; 2,2-dimethyloxypropane; dimethyl sulfoxide (DMSO); and the like. The solvent may be an organic solvent or an inorganic solvent. Furthermore, the solvent may be aqueous or nonaqueous. As will be readily appreciated by one of ordinary skill in the art, the choice of solvent will depend on the desired solubility, the nature of the active agent, and the desired release characteristics.

The amount of solvent present in the formulation will vary depending on the type of tumor (solid or soft), the solubility of active agent, the solvent chosen, and the desired form of the formulation (e.g., solution, suspension, etc.). Those of ordinary skill in the art routinely consider such factors in determining the appropriate amount of a solvent in a pharmaceutical formulation. Thus, the amount of solvent included in the pharmaceutical formulation may be established by those skilled in the art without undue experimentation.

The amount of solvent contained in the formulation is preferably from about 0.01% by volume to about 50% by volume (v/v) of formulation. It is particularly preferred that the solvent is present in an amount of from about 0.1% by volume to about 30% by volume of formulation. Most preferably, the solvent is present in an amount of from about 1% by volume to about 15% by volume of formulation. When the solvent used in the formulation is chosen from the group consisting of dimethylacetamide, dimethyl sulfoxide, 1,1-dimethyloxymethane, 2,2-dimethyloxypropane, propylene glycol, and combinations thereof, it is particularly preferred that the solvent is present in an amount of from about 0.01% by volume to about 5% by volume of the formulation. When the solvent used in the formulation is a monohydric alcohol, e.g., ethanol, it is particularly preferred that the solvent represent from about 0.01% by volume to about 15% by volume of the formulation.

C. Carrier and Optional Components

The invention is not limited with regard to the type of carrier used so long as it is a pharmaceutically acceptable carrier. Preferably, the carrier is a solution such as a sodium chloride solution (e.g., normal saline), a dextrose solution, lactated Ringer's solution, water, or a mixture thereof. The active agent, solvent, and any additional components are added to the carrier and mixed. Preferably, all components are completely dissolved in the carrier.

As will be readily appreciated by those of ordinary skill in the art, one or more additional active agents may be included in the formulations described herein. Classes of active agents suitable for inclusion in the present invention include, but are not limited to, agents selected from the group consisting of agents causing apoptosis (cell death), agents preventing RNA synthesis, agents that interfere with protein transport, alkylating agents, anesthetic agents, additional anti-angiogenic agents, antibacterial agents, antibodies, antifungal agents, antimetabolite agents, antineoplastic agents possessing known antiproliferative activity, antitumor antibiotics, antiviral agents, biologically active peptides, biologically active proteins, chemotherapeutic agents, chimeric peptides and proteins, cytokines, endostatin agents, fusion proteins, Golgi apparatus disturbing agents, interferons, monoclonal antibody toxins, oligonucleotides, pain-relieving agents, plant alkaloids, signal transduction inhibitors, signal transduction pathway inhibitors such as inhibitors of kinases and phosphatases, and combinations of any of the foregoing.

Specific examples of additional active agents include, without limitation, agents selected from the group consisting of acaricides, actinomycin-D, aldesleukin, aminoglutethimide, amsacrine, anastozole, angiostatin, L-asparaginase, avermectins, azalides, 5-azacytidine, aziridinylbenzoquinone, bafilamycin, bioallenthirn, bleomycin, bicalutamide, bredinin, bryostatin 1, buserelin, busulfan, carboplatin, carmustine, chivosazol A, chlorambucil, cisplatin, cladribine, colchicinefosfamide, copiamycin, cyclophosphamide, cyproterone, cytarabine, dacarbazine, dactinomycin, daunorubicin, deoxycoformycin, desertomycin, difficidin, diethylstilbestrol, docetaxel, doramectin, doxorubicin, doxycycline, endostatin, epirubicin, eprinmectin, estramustine, etoposide, fludarabine, fludrocortisone, 5-fluorodeoxyuridine, 5-fluorouracil, fluoxymesterone, flutamide, geldanamycin, gemcitabine, genistein, grahamimycins, goserelin, hydroxyurea, idarubicin, ifosfamide, ilimaquinone, α-interferon, irinotecan, ivermectin, leucovorin, leuprolide, levamisole, lincomycin, lomustine, mathemycin, mechlorethamine, medroxyprogesterone, megestrol, megovalicins, melphalan, mercaptopurine, mesna, methotrexate, minocycline, mithramycin, mitomycin, mitotane, mitoxantrone, moxidectin, nilutamide, nocodazole, okadaic acid, octreotide, oocydin A, oxydifficidin, paclitaxel, pentostatin, plicamycin, porfimer, procarbazine, radicicol, rapamycin, retinoic acid, rhizoxin, sirolimus, staurosporine, streptozocin, sporaviridin, streptogramin, suramin, tamoxifen, tautomycin, teniposide, testolactone, 6-thioguanine, thiotepa, tolytoxin, topotecan, tryphostins, vinblastine, vincristine, vindesine, vinorelbine, virginiamycin, wortmannin, derivatives thereof, and combinations of any of the foregoing.

The pharmaceutical formulations of the present invention are not limited with regard to the particular form used. A nonlimiting list of preferred delivery forms of the present invention includes solutions, suspensions, dispersions, emulsions, and microspheres. For systemic administration, solutions and suspensions are preferred. For local administration, any delivery form, e.g., solution, suspension, dispersion, emulsion, or microspheres, may be used.

The pharmaceutical formulation may include one or more additional components. Such additional components include, for example, antimicrobials, buffers, antioxidants, tonicity-adjusting agents, and detergents. Antimicrobial agents are used to deter the growth of microorganisms, particularly in multiple dose formulations (i.e., formulation for a multiple dose vial). Suitable antimicrobial agents include phenylmercuric nitrate, thimerosal, benzethonium chloride, benzalkonium chloride, phenol, cresol, chlorobutanol, and combinations thereof. Buffers are used primarily to stabilize a solution against potential chemical degradation resulting from a change in the formulation's pH. Suitable buffers include acid salts of citrates, acetates, and phosphates. Antioxidants are used for preservation, as many drugs are susceptible to degradation through oxidation. Examples of antioxidants include sodium bisulfite, acetone sodium bisulfite, sodium formaldehyde, sulfoxylate, thiourea, ascorbic acid, sodium salt of ethylenediamine tetraacetic acid, and storage in an inert gas (e.g., nitrogen). Tonicity-adjusting agents are used to control tonicity to ensure that the resulting formulation is not excessively hypotonic or hypertonic relative to the physiological state. Examples of tonicity agents include electrolytes (e.g. sodium chloride) and mono- or disaccharides (e.g., dextrose for monosaccharides). Examples of detergents include, for example, anionic detergents; nonionic detergents, e.g., polyoxyethylated sorbitans (available under the TWEEN® name from ICI Americas, Inc.); sorbitan esters; polysorbates; polyoxyethylene ethers (e.g., available under the TRITON® name from Union Carbide Corp., Midland Mich.); cationic and zwitterionic detergents; and combinations thereof.

The amounts of additional components that are not active agents will vary depending on the solvents chosen, desired form of the formulation, and other factors. Those of ordinary skill in the art routinely consider such factors. Thus, the amount of any particular additional component can be established by those skilled in the art without undue experimentation. Typically, the amount of any such component preferably does not exceed 10% by volume of the total formulation. More preferably, any optional component does not exceed 1% by volume of the total formulation. Most preferably, an optional component is present in an amount of from about 0.0001% by volume to about 1.0%.

The pharmaceutical formulations of the present invention may be sustained-release formulations. That is, the formulation would release the active agent over an extended period of time relative to an immediate-release or nonsustained-release formulation. It is preferred that the pharmaceutical formulations of the present invention release active agent over a time of from about 4 hours to about 24 hours. It is particularly preferred that formulations intended for local delivery be sustained-release formulations.

Sustained-release formulations generally include one or more components designed to slow or control the release of the agent over time. The invention is not limited with regard to the particular component(s) used to effect sustained release, so long as the component or components are pharmaceutically acceptable. Preferred sustained-release components include polysaccharides, salts of polysaccharides, micro spheres of polysaccharides, dextrins, gums, celluloses, gels, silicones, liposomes, and combinations thereof. It is particularly preferred that the sustained-release component be a polysaccharide. It is particularly preferred that the polysaccharide be selected from the group consisting of chitin (poly-N-acetyl-D-glucosamine), chitosan (deacetylated chitin), and combinations thereof. Derivatives of these carriers are contemplated as well, including, for example, derivatives formed by adding or removing sugar molecules (i.e. by increasing or decreasing the weight average molecular weight of the carrier). Thus, preferred carriers have a weight average molecular weight of about 500 daltons to about 100,000 daltons, more preferably of about 10,000 daltons to about 60,000 daltons.

Optimally, the component providing sustained release is covalently bonded to the active agent, thereby providing a sustained-release conjugate. For example, chitin may be covalently bound to brefeldin A, typically through the 1-OH or 13-OH moieties of brefeldin A. Methods for producing these conjugates are well known to those skilled in the art, and are described in detail in the pertinent texts and literature.

The amount of the component or components providing sustained release will vary depending on the particular active agent and other components in the formulation. The amount will also depend on other factors, such as whether the formulation is intended to contain a single dose or multiple doses, and the injectability (e.g., viscosity) of the resulting formulation. In addition, the amount should be considered in light of the environment of the target area in which the pharmaceutical formulation will be administered. For example, it is desirable that low density organs, e.g., the prostate, brain, and bladder, receive a low viscosity formulation, whereas dense tissue, e.g., solid tumors and breast tumors, receive a high viscosity pharmaceutical formulation. Those of ordinary skill in the art routine consider these and other factors in providing sustained-release formulations.

Generally, the total amount of a sustained-release component in the formulation is preferably between from about 0.01% w/v to about 50% w/v of the total formulation. It is particularly preferred that the biocompatible carrier is present in an amount of from about 0.5% w/v to about 30% w/v. Most preferably, the sustained-release component is present in an amount of from about 1% w/v to about 20% w/v. When the sustained-release component is chitin, chitosan, or a combination thereof, it is preferred that chitin, chitosan, or a combination thereof represent from about 1% to about 20% w/v of the entire formulation.

III. Methods of Treatment

The present invention also provides a method for inhibiting angiogenesis in a patient in need thereof comprising administering to the patient an effective angiogogenesis-inhibiting amount of an active agent, e.g., brefeldin A, as described herein. The method is used to treat a patient suffering from a condition, disease, or disorder that is treatable by at least partial inhibition of angiogenesis. Typically, patients suffering from arthritis, e.g., rheumatoid arthritis, psoriasis, or diabetic retinopathy, benefit from the present methods. Additionally, patients suffering from a neoplastic disease, i.e., a cellular proliferative disease, also benefit from administration of the present compositions. Generally, cellular proliferative diseases include not only sarcomas, carcinomas, lymphomas, and malignant melanomas, but also noncancerous melanomas and other benign growths caused by rapidly dividing cells.

Nonlimiting examples of cellular proliferative diseases for which the present invention is suited include adrenocortical cancer, bladder cancer, bone cancer, brain cancer, breast cancer, cervical cancer, colon cancer, colorectal cancer, endometrial cancer, esophogeal cancer, eye cancer, gallbladder cancer, gastric cancer, head and neck cancer, laryngeal cancer, liver cancer, lung cancer, melanoma, myeloproliferative disorders such as myeloma, neck cancer, nonmelanoma skin cancer, ovarian cancer, prostate cancer, pancreatic cancer, rectal cancer, and testicular cancer. Diseases for which the present invention is particularly well suited to treat include those diseases selected from the group consisting of brain cancer, bladder cancer, breast cancer, colon cancer, colorectal cancer, rectal cancer, head and neck cancer, liver cancer, lung cancer myeloma, prostate cancer, and ovarian cancer.

Although any route of administration may be used, parenteral administration, i.e., administration by injection, is preferred. Injectable formulations can be prepared in conventional forms, either as liquid solutions or suspensions; as solid forms suitable for solubilization or suspension in liquid prior to injection; or as emulsions. Preferably, sterile injectable suspensions are formulated according to techniques known in the art using suitable pharmaceutically acceptable carriers and other optional components as discussed above.

Parenteral administration may be carried out in any number of ways, but it is preferred that the use of a syringe, catheter, or similar device, be used to effect parenteral administration of the formulations described herein. The formulation may be injected systemically such that the active agent travels substantially throughout the entire bloodstream. Also, the formulation may also be injected locally to a target site, i.e., injected to a specific portion of the body for which inhibition of angiogenesis is desired. An advantage of local administration via injection is that it limits or avoids exposure of the entire body to the active agent. It must be noted that in the present context, the term local administration includes regional administration, e.g., administration of a formulation directed to a portion of the body through delivery to a blood vessel serving that portion. Local delivery may be direct, i.e., intratumoral. Local delivery may also be nearly direct, i.e., intralesional or intraperitoneal, that is, to an area that is sufficiently close to a tumor so that the active agent exhibits the desired pharmacological activity. Thus, when local delivery is desired, the pharmaceutical formulations are preferably delivered intralesionally, intratumorally, or intraperitoneally.

It is intended that, by local delivery of the presently described pharmaceutical formulations, a higher concentration of the active agent may be retained at the target site. There are several advantages to having high concentrations delivered directly at the target site. First, since the active agent is localized, there is less potential for toxicity to the patient since minimal systemic exposure occurs. Second, drug efficacy is improved since the target site is exposed to higher concentrations of drug. Third, relatively fast delivery ensures both solubility of the drug and little or no degradation of the active agent before reaching the target site. Fourth, the method is relatively noninvasive, which is ideal for unresectable tumors such as brain tumors, liver tumors, and pancreatic tumors.

With local administration, it is preferred that the pharmaceutical formulations of the present invention be directed to the target area with the assistance of computerized tomography (CT), ultrasound, or similar method in order to ensure correct placement. Once the initial dose is administered, the patient may be given other doses either immediately or after a period of time. Such a dosing schedule is easily determined by one of ordinary skill in the art once the nature of the condition, disorder, or disease, strength of the patient, expected effects of the formulation, and so forth, are taken into consideration.

The amount of the active agent administered will, of course, be dependent on the subject being treated, the subject's weight, the manner of administration, and the judgment of the prescribing physician. The amount of the active agent administered, however, will be an effective angiogenesis-inhibiting amount. Preferably, the active agent, e.g., brefeldin A, is administered in an amount of from about 0.0001 mg/kg to about 200 mg/kg (milligrams of drug per kilogram body weight of the patient), more preferably from about 0.0001 mg/kg to 120 mg/kg, still more preferably from about 0.0001 mg/kg to about 15 mg/kg, yet still more preferably from about 0.5 mg/kg to about 15 mg/kg, and most preferably from about 1 mg/kg to about 13 mg/kg. Depending on the patient's response, additional dosages within this range may be administered.

The total amount of the formulation delivered to the patient will depend upon, inter alia, the condition, disease, or disorder being treating, the type of the patient, e.g., human or animal, and the patient's body weight. Generally, however, total volumes of between about 0.1 ml to about 60 ml, and more preferably between about 0.5 ml to about 30 ml, of formulation are used. Most preferably, the total volume administered of the presently described pharmaceutical formulation is from about 1.0 ml to about 15 ml.

It is to be understood that, while the invention has been described in conjunction with the preferred specific embodiments thereof, that the description above as well as the examples that follow are intended to illustrate and not limit the scope of the invention. Other aspects, advantages, and modifications within the scope of the invention will become apparent to those of ordinary skill in the art to which the invention pertains.

All patents, patent applications, and publications mentioned herein, both supra and infra, are hereby incorporated herein by reference.

Experimental

The practice of the present invention will employ, unless otherwise indicated, conventional pharmaceutical and experimental techniques and the like, which are within the skill of the art. Such techniques are explained fully in the literature.

In the following examples, efforts have been made to ensure accuracy with respect to numbers used (e.g., amounts, temperatures, etc.) but some experimental error and deviation should be accounted for. Unless indicated otherwise, temperature is in degrees Celsius and pressure is at or near atmospheric. All reagents were obtained commercially unless otherwise indicated.

For Examples 1–3, the pharmaceutical formulations were prepared just prior to use. Various amounts of brefeldin A (BFA) (mg of drug/kg animal's body weight) were weighed out, and solvent (varying amounts of ethanol in saline) was then added. The mixtures were either vortexed (mechanical mixing) or sonicated until the drug was either completely dissolved or only a very small amount appeared to settle in the bottom the test tube.

In vivo efficacy was determined using either inbred C3H or hybrid B6D2F1 mice carrying RIF-1 (radiation induced firbrosarcoma-1) or LL/2 (Lewis lung carcinoma) tumors, respectively. The tumor cells were kept in a $CO_2/O_2$ atmosphere at 37° C., and grown in monolayers. When confluent, cells were rinsed with ice-cold phosphate buffered ethylenediamine tetraacetic acid (EDTA), followed by trypsin/EDTA treatment for about 3 minutes at 37° C. The cells were then dispersed by the addition of medium with serum and spun down using a centrifuge, then washed once in phosphate-buffered saline (PBS) prior to suspending at the desired density (cells/ml) in sterile Hank's balanced salt solution (HBSS). The cells were then inoculated subcutaneously (s.c.) with either a 100 μl or 50 μl injection on one flank of each mouse to provide the desired number of cells ($1.25 \times 10^5$, $2.5 \times 10^5$ or $5.0 \times 10^5$) per site.

Five to ten days after inoculation with the tumor cells, treatment was initiated with either solvent alone for control groups, or solvent with BFA for the treated group. The mice were treated daily for one to two weeks either intraperitoneally (i.p.) or intravenously (i.v.). The mice (weighing approximately 25 g each) were observed daily for the absence or presence of a tumor, as well as for signs of gross toxicity such as weight loss, hair loss, lethargy, and/or dehydration. The body weight for each mouse was recorded daily until the end of treatment. At the termination of treatment, mice were euthanized, and their tumors removed and stored in formalin for sectioning and staining in future studies. In some experiments, organs such as the kidney, spleen, liver, and brain were also stored in formalin (10%) for future histological analysis of organ toxicity.

EXAMPLE 1

The toxicity and efficacy of brefeldin A (BFA, 11 mg/kg) in 10% ethanol (in saline) were determined in B6D2F1 mice. On Day 0, mice were inoculated on one flank with $1.25 \times 10^5$ LL/2 tumor cells in 50 μl liquid carrier. Five days after inoculation with the tumor cells, mice were randomized into control and treated groups. The mice received daily treatments (0.2 ml, i.p.) for two weeks with either 10% ethanol in phosphate-buffered saline (control) or 10% ethanol in phosphate-buffered saline with BFA (treated). Each mouse in the treated group received a total dose of 0.28 mg of BFA daily.

All mice were observed daily for signs of gross toxicity and the absence or presence of tumor growth. In addition, all mice were weighed daily. One day following the final treatment, mice were euthanized, and kidney, spleen, liver, brain, and tumor cell inoculation sites from both control and treated groups were harvested and stored in formalin. The tissue samples were sectioned and stained with hematoxylin and eosin (H&E) for histological analysis for organ toxicity. Efficacy was determined by delay in the appearance of the tumor in the experimental group relative to control.

Figure 1:
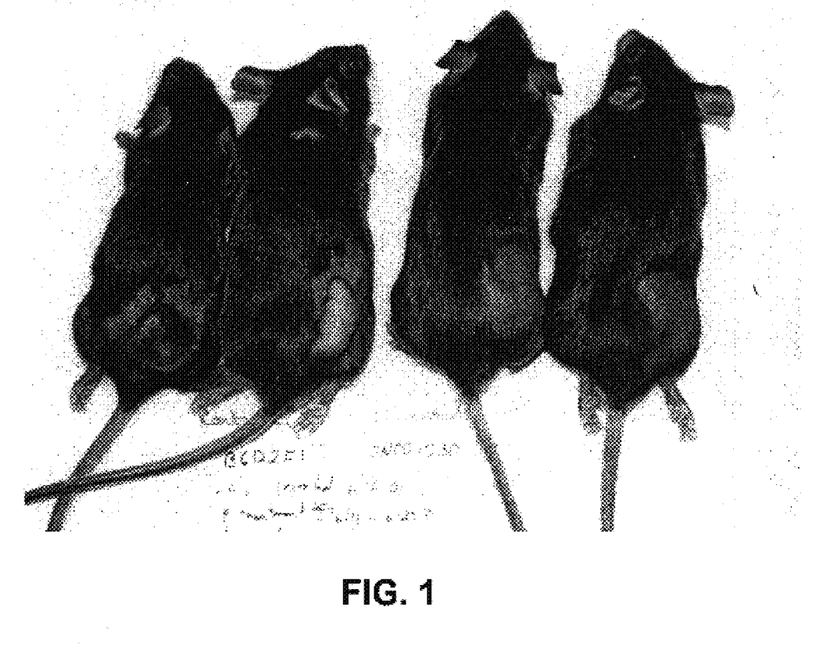
FIG. 1 is a photograph of untreated and treated mice following the experiment conducted in Example 1.

As seen in FIG. 1, no evidence of tumor was observed in the BFA-treated mice (the two mice on the right in FIG. 1). In contrast, however, control mice (the two mice on the left in the FIG. 1) grew large tumors.

Figure 2A:
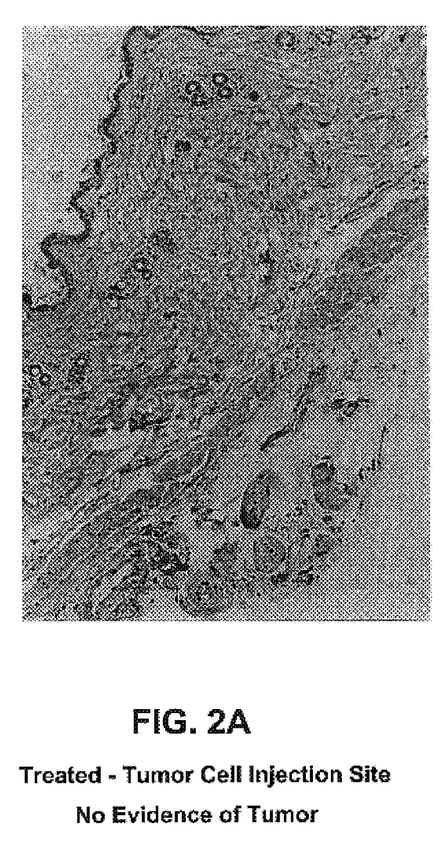
FIGS. 2A and 2B are magnified images of tissue samples of treated (FIG. 2A) and untreated (FIG. 2B) mice following the experiment conducted in Example 1.
Figure 2B:
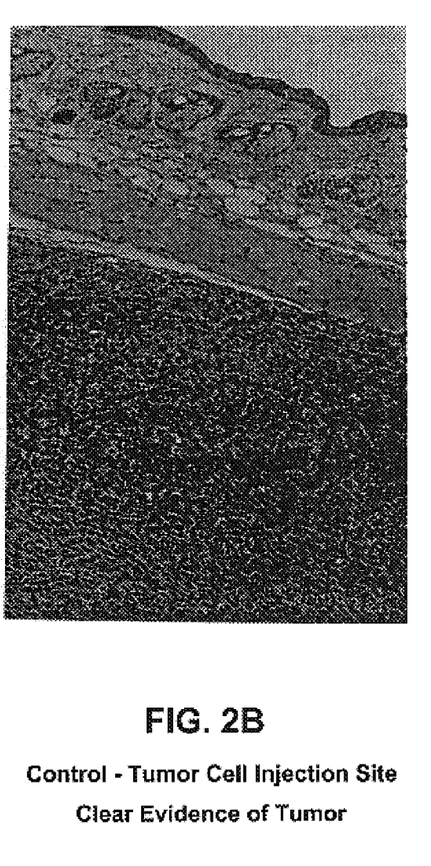

After the final treatment, skin samples from the tumor inoculation sites of a control mouse and a treated mouse were obtained and analyzed. No evidence of tumor at the injection site in mice of the treated group was found (FIG. 2A), compared with aggressive tumor growth in the control group (FIG. 2B).

Gross toxicities, such as weight loss, hair loss, lethargy, and/or dehydration, were not observed in either group. Additional analysis revealed no toxicity-related effects in the brain, kidney, liver, or spleen for either the treated or the control groups.

EXAMPLE 2

The efficacy of brefeldin A (BFA, 12 mg/kg) in 10% ethanol (in saline) was evaluated in B6D2F1 mice with a higher tumor cell burden than used in Example 1. Generally, the procedures of Example 1 were followed. On Day 0, mice were inoculated on one flank with $5.0 \times 10^5$ LL/2 tumor cells in 50 µl. Five days following tumor cell inoculation, the mice were randomized into control and treated groups. The mice then received daily treatments (0.2 ml, i.p.) for two weeks with either 10% ethanol in phosphate-buffered saline (control) or 10% ethanol in phosphate-buffered saline with BFA (treated). Each mouse in the treated group received a total daily dose of 0.3 mg BFA intraperitoneally for two weeks.

All mice were observed daily for signs of gross toxicity and the absence or presence of tumor growth. In addition, all mice were weighed daily. One day following the final treatment, mice were euthanized, and kidney, spleen, liver, brain, and tumors from both groups were harvested and stored in formalin for future histological analysis. Efficacy was determined by delay in the appearance of tumor in the experimental group relative to control.

Figure 3:
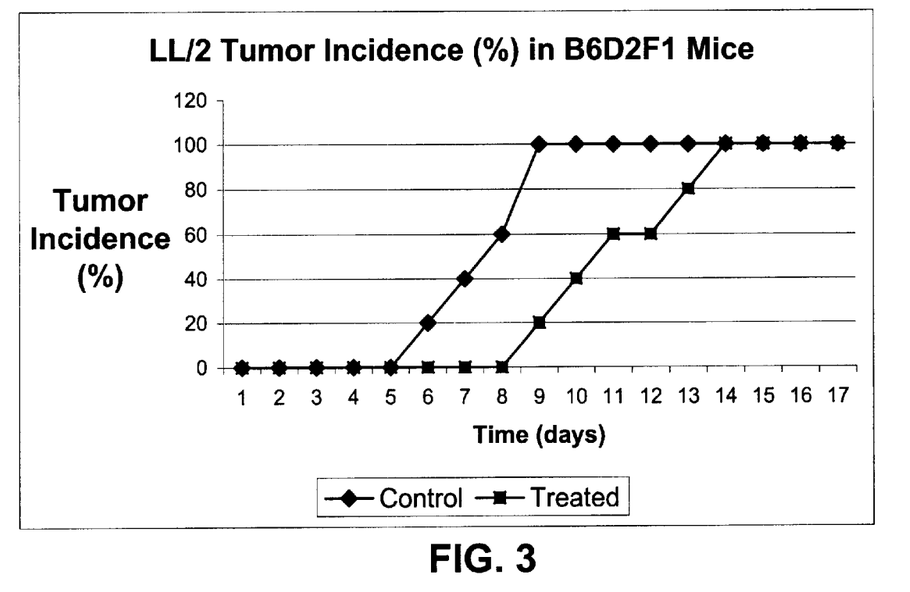
FIGS. 3 and 4 are graphs depicting some of the results obtained in Example 2.
Figure 4:
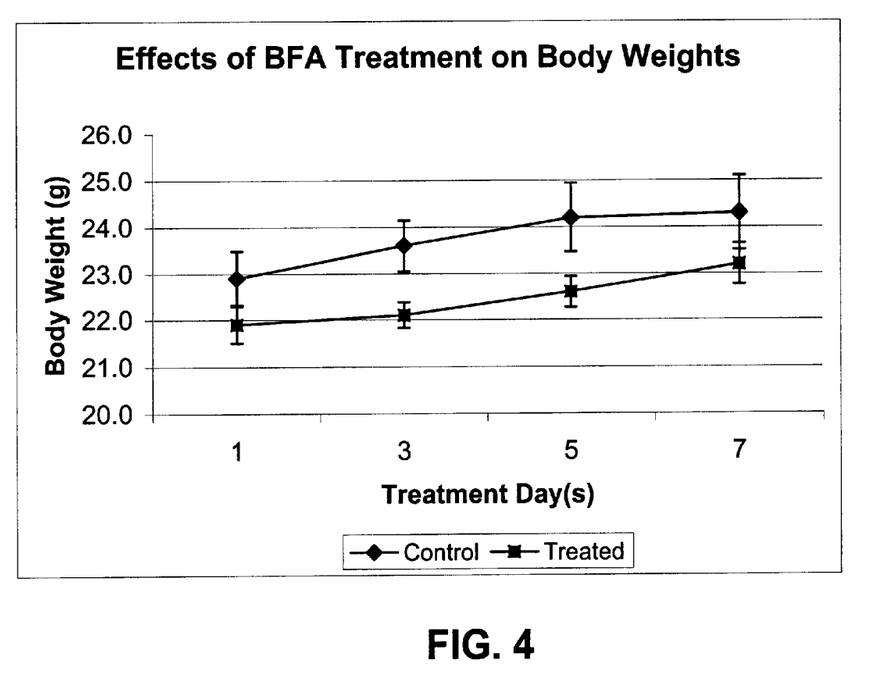

The results of the experiment were analyzed following the final day of treatment. Although tumors were observed in both groups, significant tumor growth delay was observed in the BFA treated group, as shown in FIG. 3. Furthermore, the tumors observed in the treated group were at least 25% smaller than tumors in the control group. Finally, no gross toxicity such as weight loss (FIG. 4), hair loss, or lethargy was observed.

EXAMPLE 3

The efficacy of a lower dose of BFA (8 mg/kg), in a lower concentration of ethanol (1.0%) in phosphate-buffered saline, relative to Examples 1 and 2 was determined. In addition, the dose in this example was administered intravenously, rather than intraperitoneally as in Examples 1 and 2.

On Day 0, C3H mice were inoculated on one flank (s.c.) with $2.5 \times 10^5$ RIF-1 tumor cells in 50 µl liquid carrier. Ten days following tumor cell inoculation, mice were randomized into control and treated groups. The mice received daily treatments (0.1 ml, i.v.) for eight days with either 1.0% ethanol in phosphate-buffered saline (control) or BFA (8.0 mg/kg) in 1.0% ethanol in phosphate-buffered saline (treated). Each mouse in the treated group received intravenously a total daily dose of 0.2 mg BFA for eight days.

All mice were observed daily for signs of gross toxicity and the absence or presence of tumor growth. In addition, all mice were weighed daily. One day following the final treatment, mice were euthanized, and kidney, spleen, liver, brain, and tumors from both groups were harvested and stored in formalin for future histological analysis. Efficacy was determined by tumor growth delay as evidenced by the size and appearance of the tumor in the treated group relative to control.

Figure 5:
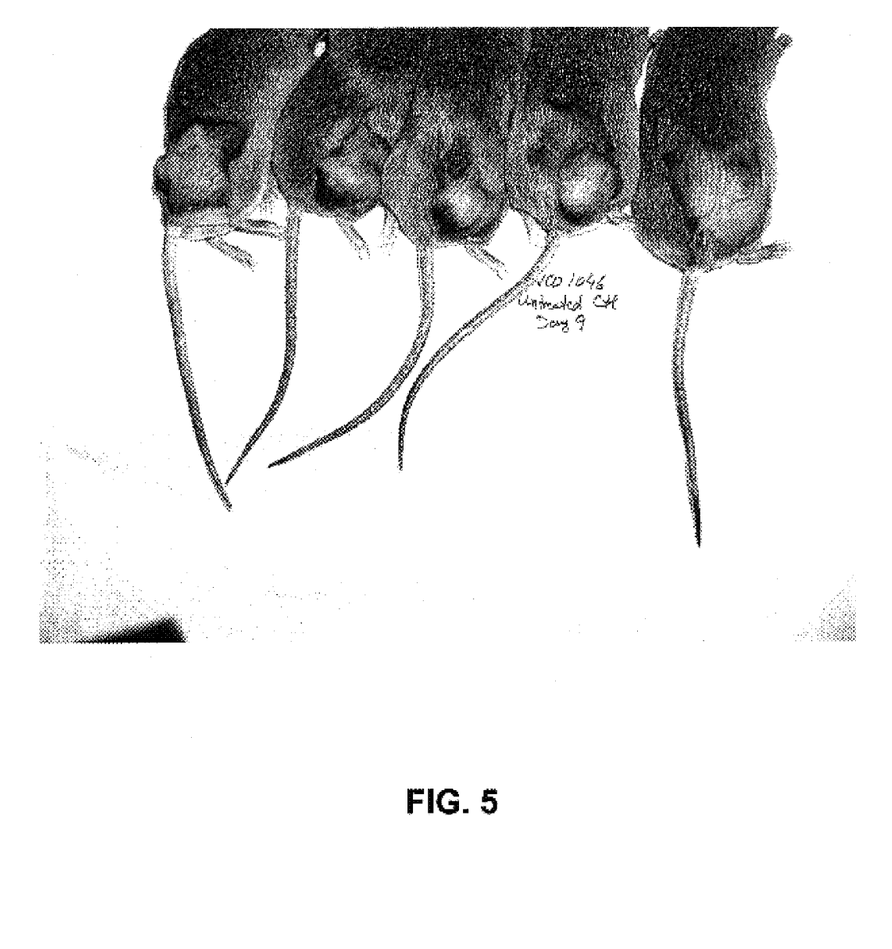
FIGS. 5 and 6 are photographs of untreated and treated mice, respectively, described in Example 3.
Figure 6:
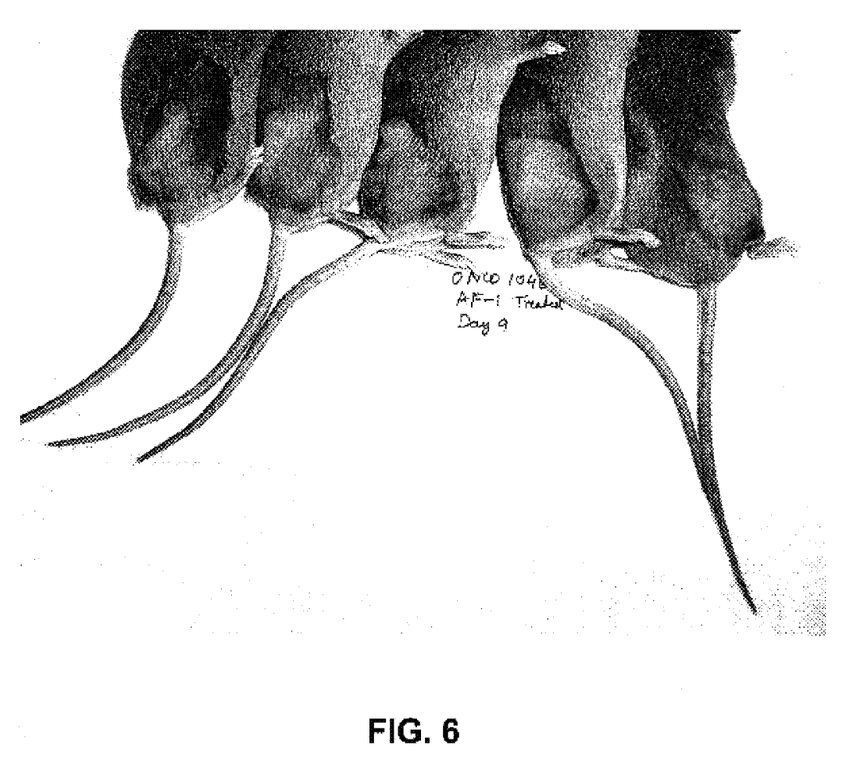

As seen in FIG. 5, the control mice grew relatively large and aggressive tumors. In contrast, the tumors observed in the treated group (FIG. 6) were significantly smaller. Furthermore, no gross toxicity was observed such as significant weight loss, hair loss, lethargy, or dehydration. Upon harvesting the tumors, it was observed that the tumors in the control group had penetrated into muscle tissue while the tumors in the treated group remained relatively localized and relatively easy to remove. In addition, qualitative assessment of the tumor sections revealed less vessel density in the tumors of treated mice compared to the control mice, thereby demonstrating at least partial inhibition of angiogenesis in the treated group.

EXAMPLE 4

The in vitro influence of brefeldin A on angiogenesis was evaluated. Human umbilical vein endothelial cells (HUVECs) were cultured in medium EBM-2 complete™ (BioWhittaker, Inc., Baltimore, Md.). Matrigel® (200 µl, synthetic basement membrane substrate) was pipetted gently to avoid air bubbles on the surface of a 48-well plate. Following application of Matrigel® substrate, the plate was placed in an incubator at 37° C. for 30 minutes to promote gelling. HUVECs were harvested from tissue culture flasks, counted, and diluted to $15 \times 10^4$/ml. The cell suspension (200 µl) was added to the Matrigel® substrate, such that the final concentration was 30,000 cells/well. Two wells/concentration were used. For evaluation of antiangiogenic activity, a 0.4 mM BFA stock (in dimethyl sulfoxide, DMSO) was diluted to a final concentration of 400, 100, 40, 4.0, and 0.4 nM before adding cells. The final DMSO concentration was 0.02%. After addition of cells and BFA on Matrigel® substrate, plates were incubated at 37° C. in a 5% $CO_2$ humidified atmosphere for 18 hours. Following incubation, HUVECs in plates were aspirated of medium, fixed and stained using a Diff-Quik® Stain Set (American Scientific Products, Inc., Huntingdon Valley, Pa.). To evaluate capillary tube formation, plates were viewed under phase contrast low magnification (10×), a photo reticule was used to define the area, and the capillary tube network was counted within the designated area. Only complete tubes that were inside the rectangle were counted.

Figure 7:
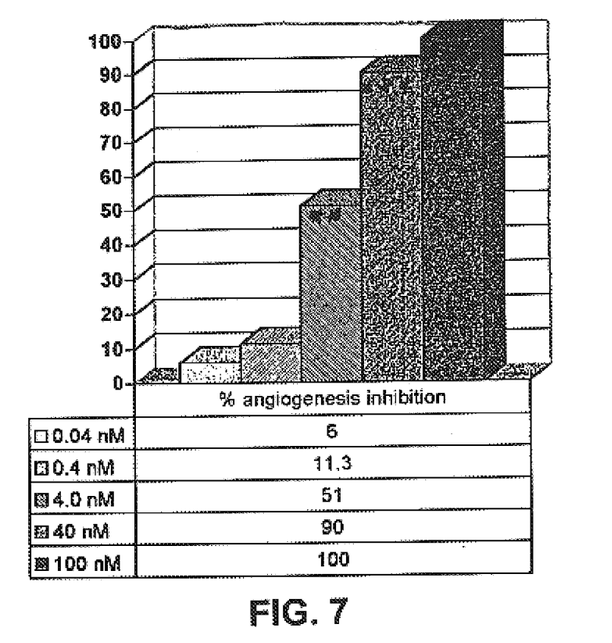
FIG. 7 is a graph illustrating anti-angiogenic effects of brefeldin A in an in vitro capillary tube formation assay with human umbilical vein endothelial cells (HUVECs), described in Example 4.

Data were expressed as percent of complete capillary tube formation relative to untreated control cultures incubated under the same conditions (control=100%). As shown in FIG. 7, bars represent the number of tubes formed in the treated sample compared to the number of tubes formed in the untreated controls. Thus, FIG. 7 shows that more than 50% inhibition of angiogenesis was observed for the tested concentrations of 4.0 nM and above. Statistical analysis of inhibition of tube formation relative to control cultures was done by Student's t-test (=P<0.001, *=P<0.0001).

EXAMPLE 5

The ex vivo influence of brefeldin A on angiogenesis was evaluated as follows. Male Sprague-Dawley rats weighing approximately 250 g were anesthetized and their thoracic aortas removed carefully to avoid damaging the vessel wall. Aortas were rinsed in serum-free endothelial cell basal medium, the surrounding adventitia removed and cleaned, and the vessels cut into two millimeter (mm) concentric rings. Each ring was embedded in freshly prepared rattail collagen. Following gelation for 30 minutes at 37° C., collagen gel cultures were transferred to 16 mm wells (4 well plate), each containing 0.5 ml of serum free (MCBD 131) medium. Brefeldin A was dissolved in DMSO and mixed with serum free medium at final concentrations of 40 nM 100 nM, 200 nM, 400 nM, and 1000 nM immediately prior to the addition of media to collagen-embedded rat aortic ring explant cultures. The final concentration of DMSO in treated and control cultures was 0.02%. Explant cultures were incubated at 35.5° C. in a 5% $CO_2$ humidified atmosphere, and the media replaced every two days over the course of the 8–10 day study. Visual counts of microvessel outgrowths from replicate explant cultures were performed using bright field microscopy during microvessel peak growth (Day 7).

Figure 8:
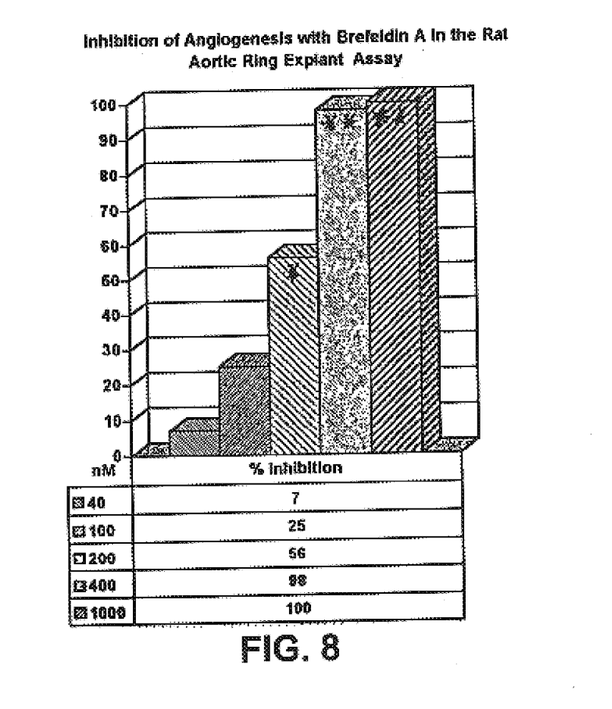
FIG. 8 is a graph depicting anti-angiogenic effects of brefeldin A in an ex vivo rat aortic ring explant assay, described in Example 5.

Data were expressed as percent inhibition of microvessel growth relative to vehicle-treated control cultures (FIG. 8). Values represent the mean number of microvessels observed in the treated group compared to the mean number of microvessels observed in the untreated control. The depicted data represent the average of three trials. As seen in FIG. 8, more than 50% inhibition of angiogenesis was observed with tested concentrations of 200 nM and above. Statistical analysis of inhibition of tube formation relative to control cultures was done by Student's t-test (*=$P<0.05$, **=$P<0.001$).

What is claimed is:

1. A pharmaceutical formulation for treating a patient in need of anti-angiogenic therapy comprising:
    a Golgi apparatus disturbing agent in an amount that is substantially noncytotoxic and effective to inhibit angiogenesis;
    a solvent; and
    a pharmaceutically acceptable carrier,
    wherein said Golgi apparatus disturbing agent is selected from the group consisting of brefeldin A, nocodazole, ilimaquinone, bafilamycin, okadaic acid, retinoic acid, and combinations thereof, and
    said solvent is selected from the group consisting of 1-butanol, 2-butanol, 3-methyl-1-butanol, 2-methyl-1-propanol, ethanol, propylene glycol, ethyl ether, ethyl formate, ethyl acetate, isobutyl acetate, isopropyl acetate, methylethyl ketone, dimethylacetamide, 1,1-dimethyloxymethane, 2,2-dimethyloxypropane, dimethylsulfoxide, and combinations thereof.

2. The pharmaceutical formulation of claim 1, wherein said Golgi apparatus disturbing agent is brefeldin A.

3. The pharmaceutical formulation of claim 1, in unit dosage form.

4. The pharmaceutical formulation of claim 3, wherein the Golgi apparatus disturbing agent is brefeldin A.

5. The pharmaceutical formulation of claim 4, wherein the brefeldin A is present in an amount that represents from about 0.0001 mg to about 15 mg per kilogram body weight of the patient in need of anti-angiogenic therapy.

6. The pharmaceutical formulation of claim 4, wherein the brefeldin A is present in the unit dosage form in an amount that represents from about 0.5 mg to about 15 mg per kilogram body weight of the patient in need of anti-angiogenic therapy.

7. The pharmaceutical formulation of claim 4, where in the brefeldin A is present in the unit dosage form in an amount that represents from about 1 mg to about 13 mg per kilogram body weight of the patient in need of anti-angiogenic therapy.

8. The pharmaceutical formulation of claim 1, wherein the solvent is ethanol.

9. The pharmaceutical formulation of claim 1, wherein the solvent is present in an amount from about 0.01% by volume to about 50% by volume (v/v) of the formulation.

10. The pharmaceutical formulation of claim 1, wherein the solvent is present in an amount from about 0.01% by volume to about 10% by volume (v/v) of the formulation.

11. The pharmaceutical formulation of claim 1, wherein the pharmaceutically acceptable carrier is selected from the group consisting of water, sodium chloride solution, lactated Ringer's solution, dextrose solution, and combinations thereof.

12. The pharmaceutical formulation of claim 1, further comprising an additional pharmacologically active agent.

13. The pharmaceutical formulation of claim 12, wherein said additional pharmacologically active agent is selected from the group consisting of acaricides, actinomycin-D, aldesleukin, aminoglutethimide, amsacrine, anastozole, angiostatin, L-asparaginase, avermectins, azalides, 5-azacytidine, aziridinylbenzoquinone, bafilamycin, bioallenthirn, bleomycin, bicalutamide, brefeldin A, bredinin, bryostatin 1, buserelin, busulfan, carboplatin, carmustine, chivosazol A, chlorambucil, cisplatin, cladribine, colchicinefosfamide, copiamycin, cyclophosphamide, cyproterone, cytarabine, dacarbazine, dactinomycin, daunorubicin, deoxycoformycin, desertomycin, difficidin, diethylstilbestrol, docetaxel, doramectin, doxorubicin, doxycycline, endostatin, epirubicin, eprinmectin, estramustine, etoposide, fludarabine, fludrocortisone, 5-fluorodeoxyuridine, 5-fluorouracil, fluoxymesterone, flutamide, geldanamycin, gemcitabine, genistein, grahamimycins, goserelin, hydroxyurea, idarubicin, ifosfamide, ilimaquinone, α-interferon, irinotecan, ivermectin, leucovorin, leuprolide, levamisole, lincomycin, lomustine, mathemycin, mechlorethamine, medroxyprogesterone, megestrol, megovalicins, melphalan, mercaptopurine, mesna, methotrexate, minocycline, mithramycin, mitomycin, mitotane, mitoxantrone, moxidectin, nilutamide, nocodazole, okadaic acid, octreotide, oocydin A, oxydifficidin, paclitaxel, pentostatin, plicamycin, porfimer, procarbazine, radicicol, rapamycin, retinoic acid, rhizoxin, sirolimus, staurosporine, streptozocin, sporaviridin, streptogramin, suramin, tamoxifen, tautomycin, teniposide, testolactone, 6-thioguanine, thiotepa, tolytoxin, topotecan, tryphostins, vinblastine, vincristine, vindesine, vinorelbine, virginiamycin, wortmannin, derivatives thereof and combinations of any of the foregoing.

14. The pharmaceutical formulation of claim 1, wherein the formulation provides a sustained-release profile in vivo.

15. The pharmaceutical formulation of claim 1, wherein the patient is a mammal.

16. The pharmaceutical formulation of claim 1, wherein the patient is a human.

17. A method of inhibiting angiogenesis in a patient in need of anti-angiogenic therapy comprising administering to the patient a pharmaceutical formulation comprising:
    a Golgi apparatus disturbing agent in an amount that is substantially noncytotoxic and effective to inhibit angiogenesis;
    a solvent; and
    a pharmaceutically acceptable carrier,
    wherein said Golgi apparatus disturbing agent is selected from the group consisting of brefeldin A, nocodazole, ilimaquinone, bafilamycin, okadaic acid, retinoic acid, and combinations thereof, and said solvent is selected from the group consisting of 1-butanol, 2-butanol, 3-methyl-1-butanol, 2-methyl-1-propanol, ethanol, propylene glycol, ethyl ether, ethyl formate, ethyl acetate, isobutyl acetate, isopropyl acetate, methylethyl ketone, dimethylacetamide, 1,1-dimethyloxymethane, 2,2-dimethyloxypropane, dimethylsulfoxide, and combinations thereof.

18. The method of claim 17, wherein the Golgi apparatus disturbing agent is brefeldin A.

19. The method of claim 17, wherein the patient is suffering from a cellular proliferative disease.

20. The method of claim 19, wherein the cellular proliferative disease is selected from the group consisting of adrenocortical cancer, bladder cancer, bone cancer, brain cancer, breast cancer, cervical cancer, colon cancer, colorectal cancer, endometrial cancer, esophogeal cancer, eye cancer, gallbladder cancer, gastric cancer, head and neck cancer, laryngeal cancer, liver cancer, lung cancer, melanoma, myeloproliferative disorders, neck cancer, non-melanoma skin cancer, ovarian cancer, prostate cancer, benign prostatic hyperplasia, pancreatic cancer, rectal cancer, and testicular cancer.

21. The method of claim 20, wherein the disease is selected from the group consisting of brain cancer, bladder cancer, breast cancer, colorectal cancer, head and neck cancer, liver cancer, lung cancer, myeloma, prostate cancer, and ovarian cancer.

22. The method of claim 17, wherein the patient is suffering from a disease selected from the group consisting of arthritis, psoriasis, and diabetic retinopathy.

23. The method of claim 17, wherein the pharmaceutical formulation is administered via injection.

24. The method of claims 23, wherein the pharmaceutical formulation is systemically injected.

25. The method of claim 24, wherein the pharmaceutical formulation is locally injected.

26. The method of claim 24, wherein the pharmaceutical formulation is injected intratumorally, intralesionally, or intraperitoneally.

27. The method of claim 17, wherein the pharmaceutical formulation is administered in the context of an ongoing dosage regime.

28. The method of claim 17, wherein the patient is a mammal.

29. The method of claim 17, wherein the patient is human.

30. The method of claim 17, wherein the solvent is ethanol.

31. The method of claim 17, wherein the solvent is present in an amount from about 0.01% volume to about 50% by volume (v/v) of the formulation.

32. The method of claim 17, wherein the solvent is present in an amount from about 0.01% by volume to about 10% by volume (v/v) of the formulation.

33. A pharmaceutical formulation for treating a patient in need of anti-angiogenic therapy comprising:

a Golgi apparatus disturbing agent in an amount that is substantially noncytotoxic and effective to inhibit angiogenesis;

a solvent; and a pharmaceutically acceptable carrier, wherein said Golgi apparatus disturbing agent is selected from the group consisting of brefeldin A, nocodazole, ilimaquinone, bafilamycin, okadaic acid, retinoic acid, and combinations thereof.

34. The pharmaceutical formulation of claim 33, wherein the Golgi apparatus disturbing agent is in the range of approximately 0.0001 wt. % to about 10 wt. %.

35. The pharmaceutical formulation of claim 34, wherein the Golgi apparatus disturbing agent is in the range of approximately 0.001 wt. % to about 1 wt. %.

36. The pharmaceutical formulation of claim 35, wherein the Golgi apparatus disturbing agent is in the range of approximately 0.01 wt. % to about 0.5 wt. %.

37. The pharmaceutical formulation of claim 34, wherein the patient is suffering from a cellular proliferative disease.

38. The pharmaceutical formulation of claim 34, in unit dosage form.

39. A method of inhibiting angiogenesis in a patient in need of anti-angiogenic therapy comprising administering to the patient a pharmaceutical formulation comprising:

a Golgi apparatus disturbing agent in an amount that is substantially noncytotoxic and effective to inhibit angiogenesis;

a solvent; and a pharmaceutically acceptable carrier, wherein said Golgi apparatus disturbing agent is selected from the group consisting of brefeldin A, nocodazole, ilimaquinone, bafilamycin, okadaic acid, retinoic acid, and combinations thereof.

40. A The method of claim 39, wherein the Golgi apparatus disturbing agent is in the range of approximately 0.0001 wt. % to about 10 wt. %.

41. The method of claim 40, wherein the Golgi apparatus disturbing agent is in the range of approximately 0.001 wt. % to about 1 wt. %.

42. The method of claim 41, wherein the Golgi apparatus disturbing agent is in the range of approximately 0.01 wt. % to about 0.5 wt. %.

43. The method of claim 39, wherein the patient is suffering from a cellular proliferative disease.

44. The method of claim 39, wherein the pharmaceutical formulation is administered by injection.

* * * * *